US005794612A

United States Patent [19]
Wachter et al.

[11] Patent Number: 5,794,612
[45] Date of Patent: Aug. 18, 1998

[54] MDI DEVICE WITH ULTRASOUND SENSOR TO DETECT AEROSOL DISPENSING

[75] Inventors: Allan Wachter; Stuart Lindsay, both of Tempe, Ariz.

[73] Assignee: Aeromax Technologies, Inc., Voorhees, N.J.

[21] Appl. No.: 832,369

[22] Filed: Apr. 2, 1997

[51] Int. Cl.⁶ .................. A61M 11/00; A62B 9/04; A62B 7/00
[52] U.S. Cl. .................. 128/200.23; 128/202.27; 128/205.23
[58] Field of Search .............. 128/200.14, 200.23, 128/202.27, 203.12, 205.23

[56] References Cited

U.S. PATENT DOCUMENTS

| | | | |
|---|---|---|---|
| 4,495,944 | 1/1985 | Brisson et al. | 128/200.23 |
| 4,984,158 | 1/1991 | Hillsman | 128/200.23 |
| 5,284,133 | 2/1994 | Burns et al. | 128/200.23 |
| 5,333,106 | 7/1994 | Lanpher et al. | 128/200.23 |
| 5,363,842 | 11/1994 | Mishelevich et al. | 128/200.23 |

Primary Examiner—Kimberly L. Asher
Attorney, Agent, or Firm—John Lezdey

[57] ABSTRACT

An intrapulmonary delivery device is provided for delivery of a propellant driven medicament. The device has an indicating system with a sensor responsive to a selected range of ultrasound, a controller associated with the sensor for signalling the detected ultrasound, a differential pressure sensor and a display for the signals. The controller is associated with a microprocessor where the signal level the duration and time of actuation is stored in memory.

20 Claims, 2 Drawing Sheets

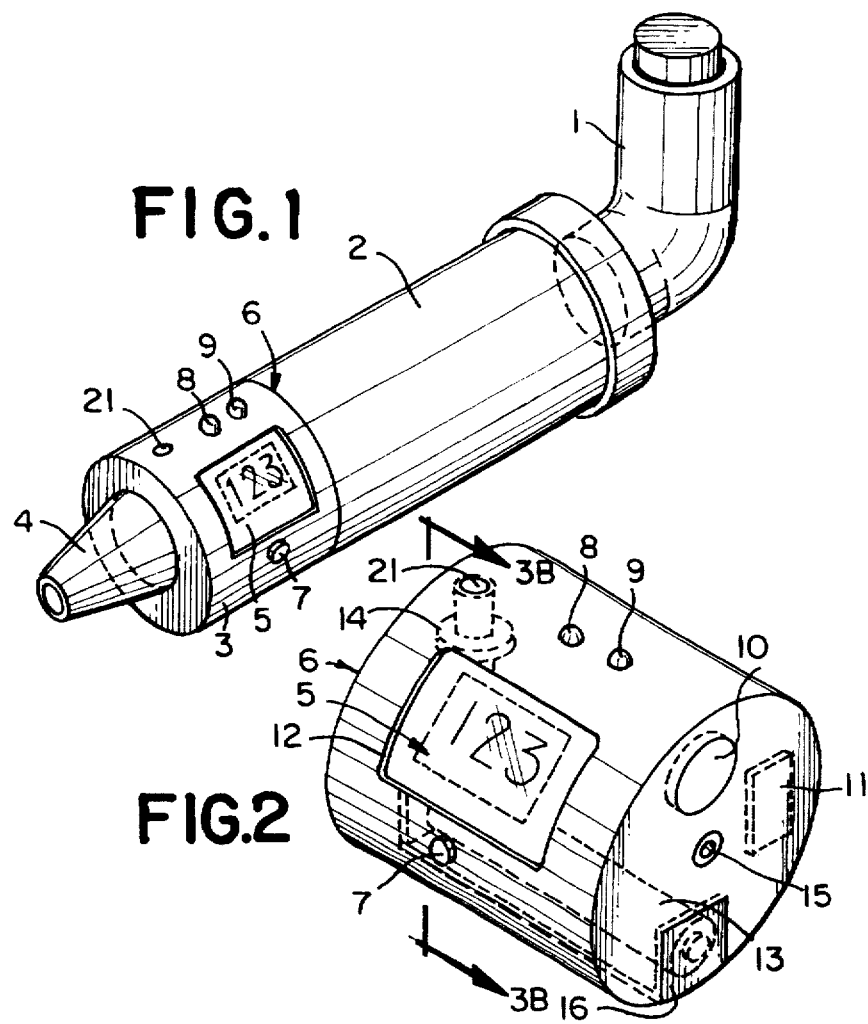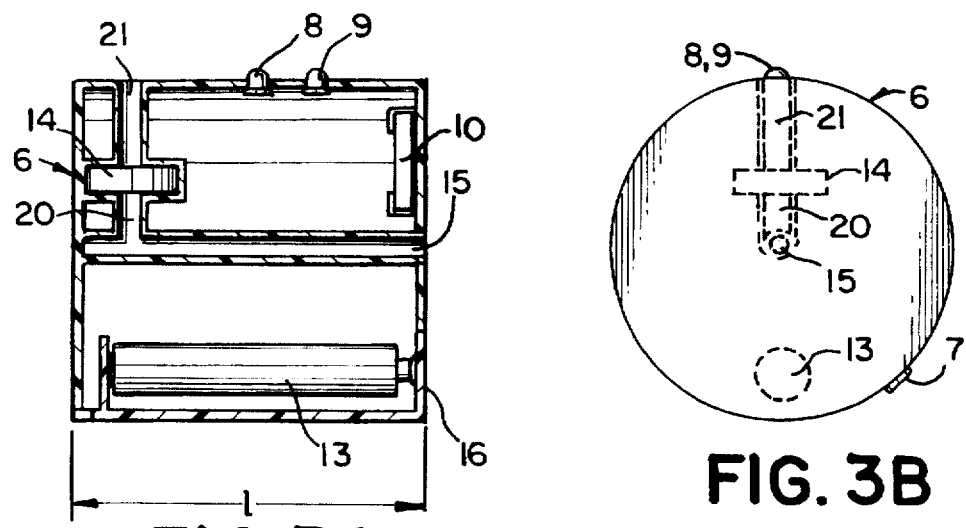

MDI DEVICE WITH ULTRASOUND SENSOR TO DETECT AEROSOL DISPENSING

FIELD OF THE INVENTION

This invention relates to a structure and method of administering precisely measured doses of a propellant driven therapeutic by inhalation. More specifically, there is provided a means for recording the administration of each dose and the amount administered.

BACKGROUND OF THE INVENTION

An accurate mechanism for delivering precise drug dose of aerosol drugs into the interior of human beings has been an objective of many workers in the art. One of the most popular aerosol delivery devices is the propellant driven metered dose inhaler (MDI) which releases metered dose of medicine upon each actuation.

U.S. Pat. No. 5,364,838 discloses an intrapulmonary device for administering insulin which contains a system for determining inspirational air flow created by a patient inhaling through the mouthpiece which has a microprocessor that collects data from an airflow detector.

U.S. Pat. No. 5,458,135 discloses a device for administering doses of powder aerosol drugs which contains a microprocessor and a key pad for inputting information to the microprocessor. The device contains a dosage recall button, a LCD which displays dates, times, puffs and dosage history.

None of the prior art devices provide a means for counting the number of doses by a change in pressure and/or indicating when a dose contains an adequate amount of drug.

When the inhalation devices are used by children or invalids, the accuracy of reported doses and/or amount of drug used in the treatment of a pulmonary disease can be questionable. An overdose or an underdose can cause a problem to the patient who is relying upon an accuracy of dosage. A need to know dosage and amount of administered drug is important in preventing underdosing or overdosing.

It is desirable that the patient be able to know if the dose is within the required range, the time when the dose was taken that the inhalation device be programmed for a specific age and disease state. Furthermore, it has been shown that few patients are able to tell when a correct dosage has been administered or if they are properly using the inhalation device.

Workers in the art have attempted to provide a metered dose of a medicant by using dry powder inhalers (DPI). Such devices normally rely on a burst of inspired air that is drawn through the unit. However, these units are disadvantaged in that the force of inspiration varies considerably from person to person. Some patients are unable to generate sufficient flow to activate the unit.

Other workers in the art have refined aqueous nebulization delivery systems. Although such systems require a continuous gas compressor, making them less portable than the MDI's and the DPI's, many nebulizers provide a low velocity aerosol which can be slowly and deeply inhaled into the lungs. Precision of dosage delivery, however, remains a serious problem and it is difficult to determine how much medicament the patient has received. Most nebulizers operate continuously during inhalation and exhalation. Dosage is dependent on the number and duration of each breath. In addition to breath frequency and duration, the flow rate, i.e., the strength of the breath that is taken from a nebulizer can effect the particle size of the dose inhaled. The patient's inhalation acts as a vacuum pump that reduces the pressure in the nebulizer. A strong breath can draw larger unwanted particles of medicant out of the nebulizer. A weak breath, on the other hand, will draw insufficient medicament from the nebulizer. There is no assurance of amount of dosage or loss of medicament.

SUMMARY OF THE INVENTION

According to the present invention, there is provided a device for the administering with a propellant a dispensable medicament powder or liquid composition for inhalation by a patient which comprise a means for delivering aerosolized doses that includes an indicating system responsive to a selected range of ultrasound to display and/or record the dispensing of the powder and/or liquid dose. The indicating system comprises a means for sensing a selected range of ultrasound, a controller having a timer and which is associated with the sensor for signalling the sensed ultrasound, a means activated by said controller for displaying and/or recording each flow rate of propellant and a differential pressure sensor. Optionally, the indicating system contains means for determining and signalling when the aerosolized dose does not contain predetermined amount of medicament.

The inhalation device can contain a pressured gas for aerosolizing the medicament or rely on the inhalation by the patient to provide the pressure within said device.

It is understood that the pressure amount is intended to mean either an exact pressure amount or a pressure range.

It is an object of the present invention to provide an intrapulmonary delivery device with a dosage recording system. It is a further object of the invention to train a patient to provide a proper inspirational flow rate of medicament.

It is another object of the invention to provide a dosage recording system for existing intrapulmonary delivery devices.

It is yet another object of the invention to provide a system for use with an intrapulmonary delivery device that can indicate dosage when activated by the patient's inhalation.

It is still another object of the invention to provide a system for delivering a precisely measured dosage propelled from an intrapulmonary delivery device.

It is a further object of the invention to provide an inhalation device which is programmable to individual needs.

It is a still further object of the invention to provide an inhalation device with a restricted flow rate to prevent excessive flow-rate of medicament.

These and other objects and advantages will be better understood from a reading of the following description of preferred embodiment and the accompanying drawings.

BRIEF DESCRIPTION OF DRAWINGS

FIG. 1 is a perspective view of an inhalation device with the indicating means of the invention;

FIG. 2 is a perspective view of an indicating device according to the invention;

FIG. 3A and 3B show the preferred channels of an inhalation device; and

DESCRIPTION OF THE PREFERRED EMBODIMENTS

Figure 4:
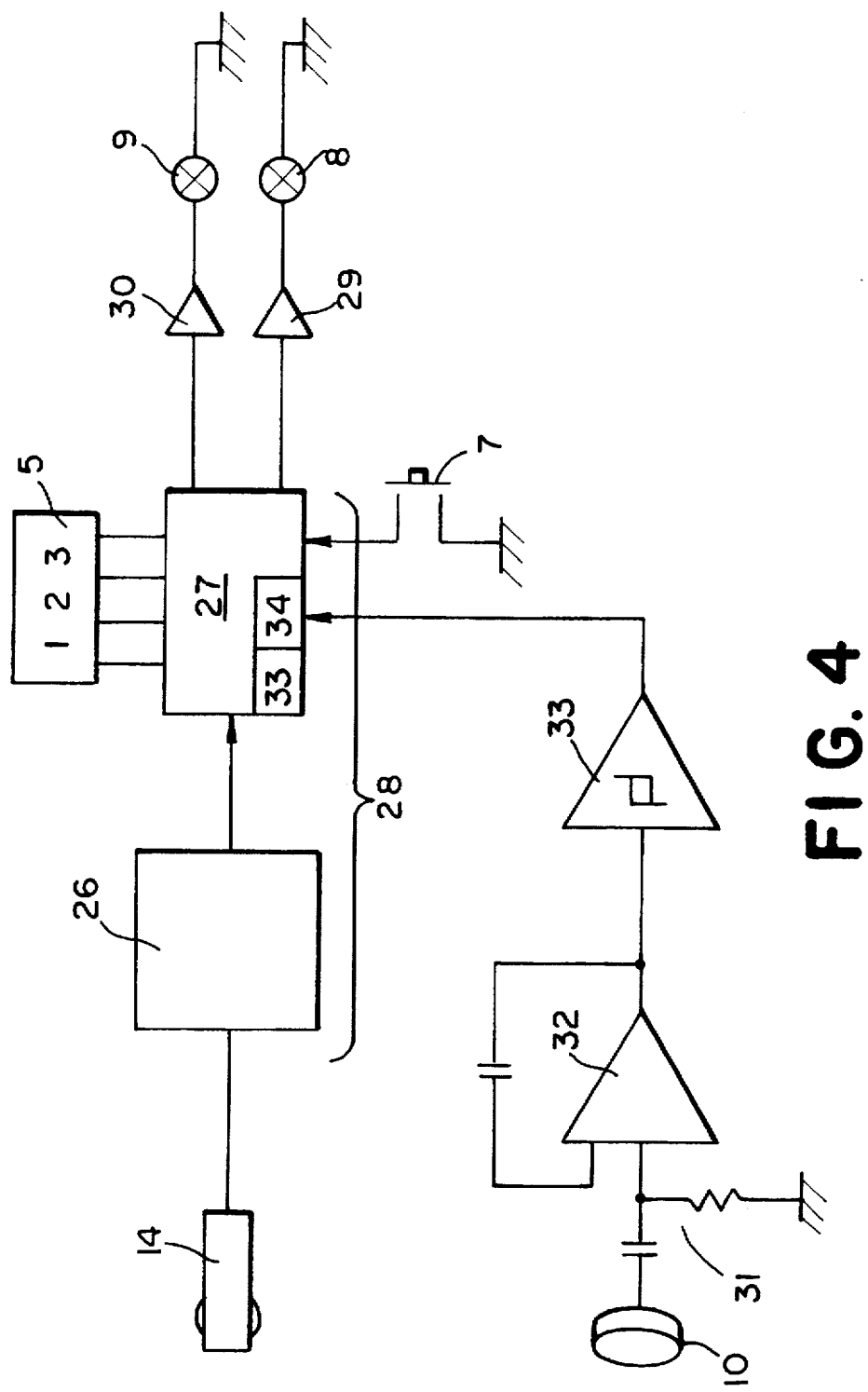
FIG. 4 shows a circuitry of the indicating device of the invention.

FIG. 1 shows the overall layout of the present invention in its preferred embodiment. Connected to an aerosol holding chamber 2 such as the Aero Chamber from Forest Pharmaceuticals of St. Louis, Mo., is a standard metered-dose-inhaler (MDI) package 1 (such as the Ventolin inhalation aerosol package from Allen and Hanbury's of Research Triangle Park, N.C.). In the present invention, a measurement and electronics package 3 is interposed between the mouthpiece 4 and the chamber 2. A liquid crystal (LC) display panel 5 shows the count of the number of actuations of the MDI as sensed remotely by an ultrasonic transducer 6 embedded in the wall of the package facing the MDI. The count may be reset on installation of a new MDI by means of the push-button switch 7. LED lamps on the top of the unit 8, 9, display the result of measurements of the flow rates of the aerosol from the chamber to the mouthpiece 4 (as described below). If the inhalation rate and timing is satisfactory, a LED 8, which is, for example, green, is illuminated. If the inhalation rate or timing is unsatisfactory, a LED 9, for example, red, is illuminated. If the red LED is illuminated, a diagnostic code is displayed on the LC display 5.

The electronics and measurement package is further illustrated in FIG. 2. An ultrasonic transducer (6) detects the burst of ultrasound that is emitted by the turbulent emission of aerosol from the MDI. An example of such a sensor would be a disk of PZT-5H material from Morgan Matroc Inc. of Cleveland Ohio. A resonant frequency is chosen that is well into the ultrasonic range. In one embodiment, this frequency could be 50,000 Hz. Very little energy is generated in this frequency range by, for example, accidental knocks and bangs, but the gas flow from the MDI produces an intense burst at this (and other) ultrasonic frequencies. In this way, actuation of the MDI is readily detected with no mechanical connection to the MDI. The detection is reliable and error free with appropriate signal conditioning. The signal conditioning is carried out in an embedded electronics package 11 which sends a digital pulse to an embedded microprocessor 12 located behind the LC display 5. The electronic package is powered by batteries 13 enclosed within the assembly and accessible via an access door 16.

Measurement of the flow rate is made using a differential pressure sensor 14 which measures the pressure drop owing to flow through a channel 15. The sensor package sends data to the microprocessor 12 where both the flow rate, and the time of the onset of the flow rate with respect to the actuation and the duration of inhalation are recorded and compared to acceptable values stored in the microprocessor's memory. Output is then sent to the LEDs 8, 9, and the LC display 5.

The electronics and measuring package of the invention can readily be adapted to any commercial inhaler. However, to optimize the invention, the channels for dispensing the medicament should be made according to the mechanism of a Poiseuille gauge.

The mechanism of a Poiseuille gauge in inhalation channels is shown in FIGS. 3A and 3B. The mechanism consists of a channel of diameter $2a$ 15 and length 1, through which the aerosol is drawn by inhalation on the mouthpiece. The relatively narrow channel serves to restrict air flow, requiring a relatively large pressure differential to achieve flow rates on the order of a liter per second, the desired optimal inhalation rate for optimal distribution of medication (Ref: Dolovich et al. Chest 80, 911 1981). This limits the tendency of the patient to inhale excessively fast. A pressure sensor 14 is embedded in the package just above the mouthpiece end of the channel. An example of a suitable sensor is the strain-gage based device made by Motorola Inc. (Mesa, Ariz.). For example, the MPX5010, gives a maximum of 5V output corresponding to a differential pressure of 75 mm Hg (i.e., approximately 10 kPa). The device measures positive pressures on the silicon diaphragm so the back of the device is exposed to the channel via a short passage 20 while the diaphragm is exposed to ambient pressure via a second channel 21.

Because of the low viscosity of air ($1.8 \times 10^{-5} m^{-1} s^{-1}$) flow at even hundreds of meters per second is still laminar. Therefore, the pressure drop ($P_2-P_1=\Delta P$) wherein $P_1$ is the pressure at the mouthpiece and $P_2$ is ambient pressure is described by the Poiseuille equation:

$$\Delta P = \frac{{}^v\!/\!_s 8 \mu l}{\Pi a^4}$$

where ${}^v\!/\!_s$=F, the flow-rate (in $m^3$ per second), μ is the viscosity ($1.8 \times 10^{-5} m^{-1} s^{-1}$) l the length of the channel and a its radius (see FIG. 3a). The pressure is in units of Pascals, Pa. A channel of 2 mm diameter (a=1 mm) and 3 cm length yields $\Delta P=10$ kPa for a flow rate of $7.6 \ ^1\!/\!_s$ ($7.6 \times 10^{-3} m^{-1}\!/\!_s$). Thus, the desired flow rate of about 0.5 to 3 l/s preferably about 1 l/s corresponds to a voltage out of the sensor of about 0.66 V.

The electronics package is illustrated in FIG. 4. The pressure sensor 14 sends a voltage out between 0 and 5V. In the example just discussed, the desired flow-rate would be indicated by a signal level of about 0.66V which occurred within about 0.5 s of the detection of an actuation and was sustained for at least 5 s from the time of the actuation (Ref: Dolovich et al. Chest 80, 911 1981). The analog signal from the pressure sensor is converted into a digital data stream by the analog to digital (A/D) converter 26. The digital stream is fed to a microprocessor 27 where the signal level and timing is compared to data stored in memory 35 built into the microprocessor 27. Timing data and a count of the number of actuations of the MDI is obtained from the ultrasound transducer 6. The output of this device is passed through a low-pass filter 31, which, together with the low sensitivity of the transducer at acoustic frequencies, eliminates a spurious excitation by mechanical shock, etc. In the example given, the low pass filter has a −3 dB frequency of 25 kHz. The signal is both amplified and integrated by the amplifier 32. The integration time is chosen to be about 20 ms, comparable to the duration of an actuation from the MDI. This further discriminates against mechanical shock, etc. The signal out of the integrator/amplifier 32 is passed to a threshold detection circuit 33 set so as to trigger only on the peak signal produced by actuation of the MDI. The digital output of the threshold detector 33 is passed to a digital input of the microprocessor 27 where it is counted so as to record an actuation and where it triggers an on-board timer 34. An example of a suitable low-power microprocessor 27 containing both timing circuitry and integrated A/D conversion as well as on-board EPROM (erasable, programmable memory) is the MC1468705G2 from Motorola Inc. of Mesa, Ariz., an integrated package is shown as 28 in FIG. 4.

The microprocessor drives the LC display 5, as well as the LED's 8, 9, via current drivers 29 and 30. The reset switch 7 is used to restart the count of actuations when a new MDI is attached. To avoid false resets, two pushes within 1s are required.

The operating algorithm is as follows: On detection of an actuation by the threshold detector 33, the count of the total number of actuations is advanced and the timer is started. If the flow-rate signal from the pressure sensor does not rise about 0.05V (in the geometry and the sensor given above) within 0.5s, the red LED 9 is illuminated and the code "LTE" for "Late" is displayed on the LCD. The display and LED is reset by pushing the reset button once. If it is accidentally pushed again within is, the red LED is again illuminated and an error message is displayed: "RYN" for "Reset, Yes/No". One push clears the error and leaves the actuation count intact, while two pushes within is on the reset button resets the actuation count. If the flow rate signal goes above 2V within 5s, the red LED 9 is illuminated and the error message "FST" for "too fast" is displayed. If the flow-rate signal falls below 0.1V in the 5s period, the red LED is illuminated and the error message "SLW" for "too slow" displayed. If the flow rate signal remains between 0.1V and 2V for 5s after the initial 0.5s wait, the green LED remains lit. If the flow rate was already above 0.5V at the moment the actuation was detected, the red LED is illuminated and the message "ELY" for "Early" is displayed. After either a reset error condition or 5.5s with no error, both LEDs are extinguished and the display returns to the actuation count.

This invention has been disclosed with specific reference to some preferred embodiments of the same, but it is to be understood that modifications and changes can be introduced by those skilled in the art without departing from the spirit and scope of the invention.

What is claimed is:

1. In a device for administering metered doses of propellant driven medicament for inhalation by a patient, said device having a mouthpiece through which the medicament passes, the improvement which comprises an indicating system having sensor means for detecting a selected range of ultrasound, controller means associated with said sensor means for signalling said detected ultrasound, said controller means having a timer;

means for recording actuations and flow rates; and
   display means for displaying said signals.

2. The device of claim 1 wherein said indicating system includes means for displaying the count of actuations.

3. The device of claim 1 wherein said indicating system includes means for comparing measured flow rates.

4. The device of claim 3 wherein the flow rate measured is made using a differential pressure.

5. The device of claim 1 wherein said controller means includes a microprocessor wherein flow rate of propellant and the time of the onset of the flow rate with respect to the actuation of propellant are recorded.

6. The device of claim 1 wherein the onset of the flow with the respect to the actuation of the device is recorded.

7. The device of claim 1 including a flow recorder wherein the duration of flow is recorded.

8. The device of claim 1 including an amplifier for said signals.

9. The device of claim 1 wherein said mouthpiece contains a strain-gauge based sensor.

10. The device of claim 1 wherein said device contains a delivery channel which delivers about 0.5 to 3 l/s of propellant.

11. The device of claim 1 wherein said device comprises a channel which restricts the flow rate for distribution of medicament which provides a pressure drop described by the equation:

$$\Delta P = \frac{v/_f 8 \mu l}{\Pi a^4}$$

wherein $v/_f = F$, the flow rate (in m³ per second), μ is the viscosity of a containing propellant ($1.8 \times 10^{-5} m^{-1} s^{-1}$), l the length of channel and a is the radius of the channel.

12. The device of claim 1 wherein there is a digital recording of actuations, a digital recording of flow-rates, a digital recording of the duration of flow, a comparison of measured flow rates with stored data and feedback to a patient on a visual display.

13. The device of claim 1 wherein said device provides feedback on timing based on visual display and error messages.

14. The device of claim 1 including a remote sensor attached to an aerosol holding chamber.

15. In a device for administering metered doses of propellant driven medicament for inhalation by a patient, said device having a mouthpiece through which the medicament passes, the improvement which comprises an indicating system having sensor means for detecting a selected range of ultrasound, controller means associated with said sensor means for signalling said detected ultrasound, said controller means having a timer;

a differential pressure sensor associated with said controller for measuring flow rate of propellant;
   means for recording actuations and flow rates; and
   display means for displaying said signals.

16. The device of claim 15 wherein said indicating system includes means for comparing measured flow rates.

17. The device of claim 16 wherein the flow rate measured is made using a differential pressure.

18. The device of claim 15 wherein said controller includes a microprocessor wherein flow rate of propellant and the time of the onset of the flow rate with respect to the actuation of propellant are recorded.

19. The device of claim 15 wherein there is a digital recording of actuations, a digital recording of flow-rates, a digital recording of the duration of flow, a comparison of measured flow rates with stored data and feedback to a patient on a visual display.

20. The device of claim 15 wherein said device comprises a channel which restricts the flow rate for distribution of medicament which provides a pressure drop described by the equation:

$$\Delta P = \frac{v/_f 8 \mu l}{\Pi a^4}$$

wherein $v/_f = F$, the flow rate (in m³ per second), μ is the viscosity of a containing propellant ($1.8 \times 10^{-5} m^{-1} s^{-1}$), l the length of channel and a is the radius of the channel.

* * * * *